(12) United States Patent
Behkish et al.

(10) Patent No.: US 11,299,443 B2
(45) Date of Patent: Apr. 12, 2022

(54) DISTILLATE PRODUCTION FROM OLEFINS IN MOVING BED REACTORS

(71) Applicant: ExxonMobil Research and Engineering Company, Annandale, NJ (US)

(72) Inventors: Arsam Behkish, Flemington, NJ (US); Lei Zhang, Basking Ridge, NJ (US); Brandon J. O'Neill, Lebanon, NJ (US); Mark A. Deimund, Jersey City, NJ (US); Alice Lin, Boonton, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 16/910,027

(22) Filed: Jun. 23, 2020

(65) Prior Publication Data

US 2021/0309587 A1 Oct. 7, 2021

Related U.S. Application Data

(60) Provisional application No. 63/004,679, filed on Apr. 3, 2020.

(51) Int. Cl.
*C07C 2/12* (2006.01)
*B01J 29/70* (2006.01)
(Continued)

(52) U.S. Cl.
CPC ............. *C07C 2/12* (2013.01); *B01J 8/005* (2013.01); *B01J 8/085* (2013.01); *B01J 29/703* (2013.01);
(Continued)

(58) Field of Classification Search
CPC .. C07C 11/06; C07C 2/12; C07C 2/04; C07C 2/10; C07C 4/06; C07C 6/04; C07C 9/14
See application file for complete search history.

(56) References Cited

U.S. PATENT DOCUMENTS 3,354,078 A 11/1967 Miale et al.
4,582,815 A 4/1986 Bowes
(Continued)

FOREIGN PATENT DOCUMENTS

EP 0552457 B1 1/1994

OTHER PUBLICATIONS

Weisz, et al.; "Superactive Crystalline Aluminosilicate Hydrocarbon Catalysts"; Journal of Catalysis, 1965, vol. 4, p. 527.
(Continued)

*Primary Examiner* — Sharon Pregler
(74) *Attorney, Agent, or Firm* — Liza Negron

(57) ABSTRACT

Systems and methods are provided for oligomerization of olefins to distillate boiling range products while also recycling naphtha boiling range olefins as part of the feed. By performing the olefin oligomerization while also recycling naphtha boiling range olefins, it has been discovered that the resulting distillate boiling range products can have an unexpected improvement in diesel combustion quality, such as an unexpected improvement in cetane rating. In order to manage coke formation and maintain consistent activity profile for the oligomerization catalyst, the reaction can be performed in a moving bed reactor. Additional temperature control can be maintained by the recycling of the naphtha boiling range portions of the oligomerization product back to the reactor.

19 Claims, 6 Drawing Sheets

(51) Int. Cl.
  *B01J 29/90* (2006.01)
  *B01J 8/08* (2006.01)
  *B01J 8/00* (2006.01)
  *B01J 38/02* (2006.01)

(52) U.S. Cl.
  CPC ............ *B01J 29/90* (2013.01); *B01J 38/02* (2013.01); *B01J 2208/00752* (2013.01); *C07C 2529/70* (2013.01)

(56) References Cited

U.S. PATENT DOCUMENTS

| | | |
|---|---|---|
| 4,968,409 A | 11/1990 | Smith |
| 5,849,976 A | 12/1998 | Gosling et al. |
| 5,916,529 A | 6/1999 | Scheuerman |
| 7,371,915 B1 | 5/2008 | Kalnes et al. |
| 7,414,167 B2 | 8/2008 | Kalnes et al. |
| 8,323,476 B2 | 12/2012 | Sadler et al. |
| 9,162,205 B2 | 10/2015 | Sprague |
| 10,188,998 B2 | 1/2019 | Behkish et al. |
| 10,351,486 B2 | 7/2019 | Behkish et al. |
| 2014/0171707 A1* | 6/2014 | Nyce .................. C07C 2/84 585/329 |
| 2017/0121237 A1* | 5/2017 | Ilias .................. C07C 1/20 |
| 2017/0137342 A1 | 5/2017 | Behkish et al. |
| 2020/0055797 A1 | 2/2020 | Deimund et al. |
| 2020/0056106 A1 | 2/2020 | Deimund et al. |
| 2021/0053891 A1* | 2/2021 | Peitz .................. B01J 23/78 |

OTHER PUBLICATIONS

Miale, et al.; "Catalysis by Crystalline Aluminosilicates IV. Attainable Catalytic Cracking Rate Constants, and Superactivity"; Journal of Catalysis, 1966, vol. 6 p. 278.

Olson, et al.; "Chemical and Physical Properties of the ZSM-5 Substitutional Series", Journal of Catalysis, 1980, vol. 61, p. 395.

* cited by examiner

DISTILLATE PRODUCTION FROM OLEFINS IN MOVING BED REACTORS

CROSS REFERENCE TO RELATED APPLICATIONS

This application claims priority to U.S. Provisional Application Ser. No. 63/004,679 filed Apr. 3, 2020, which is herein incorporated by reference in its entirety.

FIELD OF THE INVENTION

Systems and methods are provided for formation of distillate boiling range products by upgrading of olefins in moving bed reactors.

BACKGROUND OF THE INVENTION

An increasing number of hydrocarbon sources correspond to sources of methane and/or sources that are typically converted to small hydrocarbons to make the hydrocarbons suitable for further processing. One example is the increasing availability of natural gas. Natural gas typically includes a substantial portion of methane. While methane can be difficult to convert directly into products having larger carbon chains, processes for conversion of methane to methanol via syngas and then subsequently to various types of olefins correspond to mature and widely used technologies. Thus, it would be desirable to have systems and methods that can start from olefins and produce improved products, such as distillate fuel.

Moving bed reactors are a type of reactor that is potentially suitable for reactions where a fluid phase is exposed to catalyst and/or other solid particles at specified temperature and pressure conditions. Moving bed reactors provide an advantage due to the movement of the solid particles. Because the solid particles flow within the reactor, it is relatively easy to withdraw catalyst from a moving bed reactor on a periodic basis to regenerate the catalyst.

Although moving bed reactors can facilitate catalyst regeneration, transfer of multiple phases between moving bed reactors can present difficulties. In particular, moving bed reactors are not conventionally used in situations where a three phase, e.g., gas/liquid/solid, co-current flow is transferred from a first moving bed reactor to a second moving bed reactor. Because each phase of the three-phase flow has different flow properties, attempting to transfer a three-phase flow by conventional methods can result in uneven distribution of one or more flow phases. Such uneven distribution can lead to substantially reduced activity, temperature spikes, increased catalyst deactivation, and/or various other poor performance characteristics. Additionally, conventional methods of transferring a three-phase flow can suffer from limits on the ability to independently control the input flow rate of each phase into the reactor.

One option for overcoming the difficulties with managing co-current flow in a moving bed reactor is to use a counter-current flow reactor, where the direction of travel for the solid particles is the opposite of the direction of travel for the fluid phases. U.S. Pat. Nos. 4,968,409 and 5,916,529 provide examples of moving bed reactors designed for counter-current flow. The reactors include a distributor that corresponds to a cone for guiding the catalyst particles into a pipe as the catalyst moves down through the reactor. The cone distributor includes openings to allow gas to pass through the cone. The cone distributor also includes liquid conduits to transfer fluid from a reservoir up to the catalyst in the cone distributor. While a counter-current flow reactor can handle a three-phase flow, managing the three-phase flow is difficult. For example, the flow rates for each phase need to be balanced to avoid flooding of the reactor. Additionally, the residence time for contact between the liquid and the catalyst particles is relatively high, so reactions requiring a short contact time between the liquid and the solid phases are not suitable for this type of counter-current reactor configuration.

European Patent Application EP 0552457 describes another example of a counter-current moving bed reactor configuration.

U.S. Pat. Nos. 7,371,915 and 7,414,167 describe co-current moving bed reactor systems for conversion of oxygenates to propylene. Because the conversion reaction converts low molecular weight oxygenates to propylene, liquid is not formed in the reactors.

U.S. Pat. No. 8,323,476 describes moving bed hydroprocessing reactors for hydroprocessing of liquid feeds. The amount of hydrogen introduced into the reactors is limited so that a continuous liquid phase is maintained within the hydroprocessing reactors. The liquid is contacted with the solids in a radial flow configuration.

U.S. Pat. No. 5,849,976 describes a moving bed solid catalyst hydrocarbon alkylation process. The reaction zone is operated at liquid phase conditions.

U.S. Pat. No. 9,162,205 describes a co-current moving bed reactor system for contacting fluids with adsorbent particles. Due to the nature of an adsorbent/desorbent system, maldistribution of fluid flow within the reactor may lead to reduced performance, but does not otherwise result in problems due to excessive reaction of fluids with catalyst particles.

U.S. Patent Application Publication 2017/0121237 describes a two reactor system for conversion of oxygenates to naphtha and distillate. A first reactor is used to convert the oxygenates to a mixture that includes olefins. After passing through a separation stage, at least a portion of the olefins are then passed into a second reactor for oligomerization of olefins to form naphtha and distillate boiling range compounds.

U.S. Patent Application Publication 2017/0137342 describes multi-phase separators for use in producing oxygenates and olefins from hydrocarbons. The multi-phase separators are described as being suitable for use in moving bed reactors.

What is needed are systems and methods to enable transfer of a co-current three-phase flow from one moving bed reactor to another moving bed reactor when performing reactions, such conversion of oxygenates to distillate boiling range compounds, where it is desirable to control contact time of fluids with catalyst while also managing flow uniformity. This can include having the ability to separate a three-phase flow so that each phase can be separately introduced at a controlled rate. This can further include introducing each phase in a to manner that results in substantially uniform mixing of the phases.

SUMMARY OF THE INVENTION

In an aspect, a method for upgrading a feed to form distillate boiling range compounds is provided. The method includes passing a catalyst flow comprising an olefin oligomerization catalyst into a first moving bed reactor of a plurality of serially connected moving bed reactors. The olefin oligomerization catalyst can include a 1-D 10-member ring zeolite. The method further includes exposing an olefin-containing feed comprising $C_3$-$C_8$ olefins and a recycle stream comprising at least 20 wt % $C_{5+}$ olefins to the catalyst flow in the plurality of moving bed reactors under olefin oligomerization conditions to form an oligomerized effluent. The olefin oligomerization conditions can correspond to substantially adiabatic operation of the plurality of moving bed reactors. The olefin oligomerization conditions can further include an average reactor temperature of 170° C.-190° C. The method can further include separating the oligomerized effluent to form a distillate boiling range fraction and one or more lower boiling fractions, the one or more lower boiling fractions comprising the recycle stream.

DETAILED DESCRIPTION OF THE EMBODIMENTS

Figure 1:
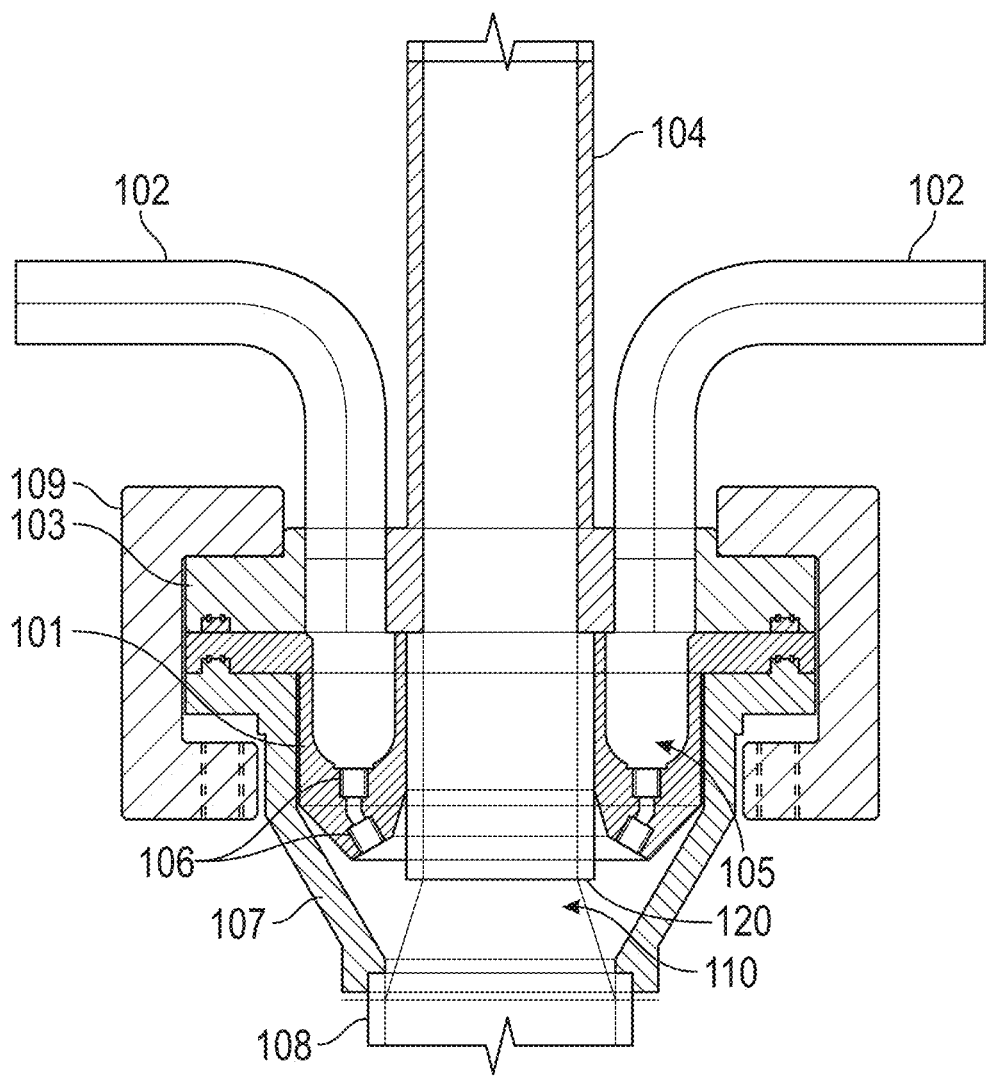
FIG. 1 shows a side view of an example of a feed distribution apparatus.

All numerical values within the detailed description and the claims herein are modified by "about" or "approximately" the indicated value, and take into account experimental error and variations that would be expected by a person having ordinary skill in the art.

Overview

In various aspects, systems and methods are provided for oligomerization of olefins to distillate boiling range products while also recycling naphtha boiling range olefins as part of the feed. By performing the olefin oligomerization while also recycling naphtha boiling range olefins, it has been discovered that the resulting distillate boiling range products can have an unexpected improvement in diesel combustion quality, such as an unexpected improvement in cetane rating. In order to manage coke formation and maintain consistent activity profile for the oligomerization catalyst, the reaction can be performed in a moving bed reactor. Additional temperature control can be maintained by the recycling of the naphtha boiling range portions of the oligomerization product back to the reactor.

In some aspects, the olefin feedstock for oligomerization can primarily include $C_{3+}$ olefins, such as $C_3$-$C_6$ olefins. The content of $C_2$ olefins and water in the feedstock can also be reduced or minimized. In such aspects, the catalyst can include a zeotype framework having a 1-D, 10-member ring structure as the largest pore channel, such as a catalyst including an MRE zeolite framework.

Oligomerization of olefins to form distillate fuels can pose a variety of challenges. Many of the challenges are related to selecting catalysts and corresponding reaction conditions that allow some oligomerization to occur, but that also stop oligomerization at a desired chain length to form distillate boiling range compounds. While some combinations of catalysts and reaction conditions have been identified that result in production of distillate boiling range compounds, the yield of distillate boiling range compounds can tend be low. This can make the production cost of distillates from olefins impractical at a commercial scale. Other challenges are related to achieving a commercial scale run length. Even for combinations of catalysts and reaction conditions are available that can allow for production of distillate fuels, such combinations can also tend to result in rapid catalyst deactivation, so that it is difficult to achieve desirable commercial scale run lengths in fixed bed reactors.

Still other challenges can be related to the highly exothermic nature of oligomerizing olefins to form distillate boiling range compounds. Due to practical considerations, it is desirable to limit the temperature gradient across an olefin oligomerization reactor to roughly 85° C. or less (~150° F. or less). In addition to maintaining control over the reaction conditions, limiting the temperature gradient is beneficial to reduce or minimize cracking of any distillate compounds formed by oligomerization. Because of the exothermic nature of olefin oligomerization, the limit on temperature gradient across a reactor constrains the size of a reactor and/or the space velocity within a reactor. As a result, managing heat generated during oligomerization of olefins can pose significant challenges.

Using a plurality of moving bed reactor stages can mitigate or minimize such heat management difficulties. For example, a plurality of moving bed reactors can be used to perform the oligomerization reactions. The reactors can be sized and/or operating conditions can be selected so that the amount of temperature increase across a single reactor is less than a target value, such as having a temperature rise of 60° C. or less across a reactor, or 50° C. or less, or 40° C. or less, such as down to a temperature gradient across the reactor of 5° C. or possibly still lower. An initial olefin-containing feed can be passed into the first reactor. The plurality of moving bed reactors can then be used to facilitate oligomerization of the resulting olefins to form distillate boiling range products while avoiding excessive heating within any single reactor.

Another form of temperature control can be to use a recycle stream that includes heavier olefins. The heavier olefins can correspond to naphtha boiling range olefins, such as olefins having a boiling range of roughly $C_5$ (boiling point of roughly 30° C. or more) to roughly 165° C. The oligomerization reaction between only light olefins ($C_2$-$C_4$) is more exothermic than oligomerization reactions that involve heavier olefins ($C_{5+}$). At the beginning of the first reactor stage, only light olefins are present in the feed. Thus, without recycle of heavy olefins, the most exothermic part of the reaction environment would be the beginning portions of the first reactor. By adding a heavy olefin recycle to the feed, the exotherm at the beginning of the first reactor can be mitigated.

In addition to assisting with temperature control, it has been unexpectedly discovered that recycle of heavy olefins, when performed under adiabatic conditions, results in an increase in the cetane value of the distillate produced by the oligomerization reaction. It is noted that recycle of naphtha boiling range alkanes as a diluent does not provide a cetane benefit. Additionally, it is believed that recycle of heavier olefins under isothermal conditions also does not provide the cetane benefit. It is unexpected that recycle of heavier olefins under adiabatic conditions provides a cetane benefit that cannot be realized under isothermal reaction conditions. It is noted that commercial scale reactors typically operate under substantially adiabatic conditions. This is due in part to the large diameter of commercial scale reactors, so that the ratio of reactor wall surface area to volume is relatively small.

This is in contrast to pilot scale reactors (1 inch diameter or less), where the small reactor diameter results in a high ratio of reactor wall surface area to interior volume. In such reactors, heat loss through the reactor walls can be significant relative to the heat generated by reaction within the reactor volume. Thus, in such reactors, isothermal operation is commonly used to provide a controlled operating environment. For the examples described herein, pilot scale reactions were performed under adiabatic conditions rather than isothermal conditions, in order to more closely replicate the conditions used in a commercial scale reactor.

Other difficulties can be related to maintaining catalyst activity during olefin oligomerization to distillate boiling range compounds. Without being bound by any particular theory, it is believed that there are two primary modes of catalyst deactivation for the zeotype catalysts used in olefin oligomerization. One type of deactivation is due to coke formation on the catalyst. As coke accumulates, it is believed that active sites can be blocked, resulting in lower catalyst activity. Fortunately, such coke can be removed by regeneration at high temperature, which can restore a substantial portion (such as up to all) of the activity loss due to coke formation.

Another type of deactivation can be related to exposure of the oligomerization catalyst to water. If sufficient water is present in the reaction environment, the oligomerization catalyst can be exposed to "steaming" conditions that result in catalyst deactivation. This type of catalyst deactivation can be reduced or minimized by using an olefin-containing feed with a relatively low content of water.

Using a plurality of moving bed reactors can further reduce or minimize the impact of both of the above types of catalyst deactivation. With regard to deactivation due to coking, the size of a moving bed reactor can be selected relative to the expected velocity of catalyst within the moving bed, so that the catalyst can be regenerated with a desired frequency. This can maintain coke on catalyst at less than or equal to a target level. With regard to deactivation due to steaming, using a moving bed reactor system means that only the catalyst currently participating in a conversion or oligomerization reaction is exposed to steam. When not inside a moving bed reactor, the catalyst can be disengaged from the liquid phase and/or gas phase portions of the flow. Catalyst can also be replaced at a convenient rate, so that the average steaming exposure of the catalyst is less than a target value. Thus, using a plurality of moving bed reactors can both reduce the amount of catalyst exposure to steam relative to the amount of feed processed, and can also allow for control over the average steam exposure prior to replacement of the catalyst particles. Additionally, without being bound by any particular theory, it is also believed that the coke profile of the catalyst within the reactor assists with protecting the catalyst from steam exposure. By using a moving bed reactor, coke accumulates on the catalyst as the catalyst moves through the reactor. Thus, as the temperature of the catalyst increases as it moves down through the reactor, the accumulation of coke mitigates any increased steaming exposure that would be caused by the increased temperature.

In this discussion, distillate boiling range compounds or products correspond to compounds or products having a boiling range of roughly 165° C. to roughly 350° C. Naphtha boiling compounds or products correspond to compounds or products having a boiling range of roughly 30° C. to 165° C. A distillate boiling range fraction corresponds to a fraction including 80 wt % or more of distillate boiling range compounds, or 90 wt % or more, such as up to 100 wt %. A naphtha boiling range fraction corresponds to a fraction comprising 80 wt % or more of naphtha boiling range compounds, or 90 wt % or more, such as up to 100 wt %.

In this discussion, the "solids volume" within a reactor is defined as the volume that receives solid catalyst particles to form the moving bed. In various aspects, the solid particles are introduced at or near the top of the solids volume, and optionally form a cone at the angle of repose for the solid particles. The solids volume includes the solids exit volume, where the mixture of solids, liquid, and any remaining gas are stripped from the solids using a stripping gas.

In some aspects, the bottom of the solids exit volume corresponds to the bottom of the solids volume. In other aspects, the bottom of the solids volume can correspond to the bottom of the exit port(s) for the stripping gas used in the solids exit volume. In this discussion, the reactor volume is defined to be the same as the solids volume.

In this discussion, the "reaction zone volume" corresponds to a region within the solids volume. The top of the reaction zone volume corresponds to the base of the cone that forms at the angle of repose of the solid particles in the solids volume. The bottom of the reaction zone volume corresponds to the beginning or top of the solids exit volume, where the solids are contacted with stripping gas. The top of the solids exit volume can be defined based on a change in the geometry, such as the transition from a cylinder or annular shape to a cone shape, or the top of the solids exit volume can correspond to the top of the exit port(s) for the stripping gas used in the solids exit volume.

In this discussion, operating a reactor to have a majority of the liquid travel axially with the solid particles can be characterized based on one or more of the following features. In some aspects, 40 vol % or more (or 50 vol % or more) of the liquid that contacts the solid particles in the reactor can be initially brought into contact with the solid particles in the top 20% of the volume occupied by the solid particles, such as up to substantially all of the liquid. In other words, regardless of the length of the contact time with the particles, the initial contact can be in the top 20% of the volume occupied by the solid particles. In many aspects, this will have substantial overlap with the top 20% of the solids volume, but the top 20% of the volume occupied by the solid particles can differ from the top 20% of the reaction zone volume in the reactor if there is substantial distance between the top level of the solid particles and the top of the reactor. By definition, any liquid that first comes into contact with a top surface of the catalyst bed in the moving bed reactor corresponds to liquid that first contacts the top 20% of the volume occupied by the solid particles.

Additionally or alternately, in some aspects 40 vol % or more (or 50 vol % or more) of the liquid that contacts the solid particles can be separated from the solid particles in the bottom 20% of the volume occupied by the solid particles, such as up to substantially all of the liquid. In many aspects, this will have substantial overlap with the bottom 20% of the reactor volume, but the bottom 20% of the volume occupied by the solid particles can differ from the bottom 20% of the volume in the reactor if there is substantial distance between the bottom level of the solid particles and the bottom of the reactor volume.

It is noted that "top" and "bottom" are relative to the direction of the co-current flow of liquid and solid particles within the reactor. In various aspects, it can be convenient to align the direction of flow with the direction of gravitational force, in order to reduce or minimize maldistribution of liquid relative to the solid particles due to gravitational pull. However, if a reactor is oriented in another manner, the "top" and "bottom" of the solid particle bed can be defined so that the "top" corresponds to where solid particles are added to the bed and the "bottom" corresponds to where solid particles are removed from the bed (such as by exiting the reactor and passing into a transfer pipe). It is noted that in an upflow configuration, this would result in the "top" of the moving bed being closer to the bottom of the reactor, while the "bottom" of the moving bed would be closer to the top of the reactor.

In some aspects, one or more moving bed reactors can be operated with a three-phase flow. In this discussion, operating a moving bed reactor with a three-phase flow corresponds to operating a reactor where 45 vol %-70 vol %, or 50 vol % to 70 vol % of the reaction zone volume corresponds to a solid (particles) phase; 10 vol % or more of the reactor volume corresponds to a liquid phase, such as 10 vol % to 45 vol %, or 20 vol % to 45 vol %, or 10 vol % to 35 vol %, or 20 vol % to 35 vol %, or 10 vol % to 30 vol %, or 10 vol % to 25 vol %; and 5 vol % or more of the reactor volume corresponds to a gas phase, such as 5 vol % to 40 vol %, or 10 vol % to 40 vol %, or 5 vol % to 35 vol %, or 5 vol % to 30 vol %, or 10 vol % to 30 vol %, or 5 vol % to 25 vol %, or 5 vol % to 20 vol %.

In this discussion, fluid communication is defined as the ability for vapor and liquid to move between two process elements. Vapor communication is defined as the ability for vapor to move between two process elements, while having reduced, limited, or optionally no movement of liquid between such process elements. Solids flow communication is defined as the ability for solid particles to move between two process elements, which typically means that fluid communication is also possible.

Feedstock and Products

In various aspects, an olefin-containing feed can be oligomerized to form distillate boiling range compounds. The oligomerization process can be facilitated by using an olefin-containing feed having a desirable distribution of olefins and/or a desirably low content of water.

The olefin-containing feed can be a mixture of olefins that includes $C_2$-$C_8$ olefins (i.e., a mixture of olefins ranging from olefins containing 2 carbons, such as ethylene, to olefins containing 8 carbons, such as 1-octene). It is acceptable for $C_{9+}$ olefins to be in the feed, such as 5.0 wt % or less relative to the weight of olefins in the olefin-containing feed. However, it is typically less desirable to include $C_{9+}$ olefins, as such olefins are already relatively close to the distillate boiling range. Optionally but preferably, 60 wt % or more, or 70 wt % or more, or 80 wt % or more of the olefins in the olefin-containing feed can correspond to $C_3$-$C_5$ olefins, such as up to 90 wt % or possibly still higher. Additionally, the ethylene ($C_2$ olefin) content can correspond to 5.0 wt % or less of the olefins in the olefin-containing feed.

The olefin-containing feed can contain 30 wt % or more of olefins, or 50 wt % or more, or 70 wt % or more, or 90 wt % or more, or 95 wt % or more, such as up to being substantially composed of olefins. Preferably, the water content of the olefin-containing feed can be 5.0 wt % or less, or 1.0 wt % or less, such as down to having substantially no water (0.1 wt % or less). By reducing or minimizing the water content of the olefin-containing feed, the amount of catalyst deactivation due to steaming can be reduced or minimized. Preferably, the organic oxygenate content of the olefin-containing feed can be 1.0 wt % or less. Under olefin oligomerization conditions, organic oxygenates (such as methanol) can react rapidly to generate heat and water. This can both modify the temperature profile within the reactor and increase catalyst deactivation due to steaming. Optionally, the olefin-containing feed can also include various diluent gases. Diluent gases can include gases that are substantially non-reactive under the olefin oligomerization conditions. Such diluent gases can include $N_2$. Other examples of diluent gases are alkanes, such as $C_1$-$C_4$ alkanes.

In addition to fresh feed, one or more recycle streams and/or co-feeds can be introduced into the oligomerization reactor. For example, since the goal is to make distillate boiling range compounds, a portion of the effluent that boils in the naphtha boiling range can be recycled back to the reactor. For example, a recycle portion can correspond to a portion of the effluent that boils at 165° C. or less, such as a portion that boils between 30° C.-165° C. This roughly corresponds to $C_{5+}$ hydrocarbons that would be included in a naphtha or gasoline fraction. In some aspects, the recycle portion can include 90 wt % or more of compounds with a boiling point of 165° C. or less, or 95 wt % or more, such as up to having substantially all compounds in the recycle portion have a boiling point of 165° C. or less. In some aspects, the recycle portion can include 90 wt % or more of compounds with a boiling point of 30° C. to 165° C., or 95 wt % or more. Optionally, portions of the effluent that boil below the naphtha boiling range can also be recycled.

In addition to recycling a portion of the effluent, a non-reactive co-feed can be introduced with the fresh feed, such as a co-feed of naphtha boiling range alkanes ($C_5$-165° C.). A co-feed of naphtha boiling range alkanes can further assist with quenching the exothermic reaction. In aspects where a non-reactive co-feed is used, the volume ratio of recycled effluent to co-feed can range from 0.1 to 10, or 0.1 to 5.0, or 0.2 to 10, or 0.2 to 5.0, or 0.5 to 10, or 0.5 to 5.0, or 1.0 to 10, or 1.0 to 5.0.

It is noted that reacting two olefins by oligomerization results in an oligomerized product that corresponds to another olefin. Thus, the composition of the recycled portion of effluent is dependent on the nature of the feed. To the degree that the feed is composed substantially of olefins, the recycled effluent will also be substantially composed of olefins. Similarly, to the degree that the feed includes alkanes, the recycled effluent will also contain a portion of alkanes. In aspects where the recycle stream is derived from the oligomerization effluent, the recycle stream can also include olefins. For example, the recycle stream can include 20 wt % or more of olefins relative to a weight of the recycle stream, or 40 wt % or more, or 60 wt % or more, such as up to being substantially entirely composed of olefins (~100 wt %). In aspects where only naphtha boiling range compounds are recycled, substantially all of the olefins can correspond to $C_{5+}$ olefins. In aspects where lighter portions of the effluent are also recycled, a portion of the olefins can correspond to $C_{5+}$ olefins, or $C_{6+}$ olefins. For example, the recycle stream can include 20 wt % or more of $C_{5+}$ olefins relative to a weight of the recycle stream, or 40 wt % or more, or 60 wt % or more, such as up to being substantially entirely composed (~100 wt %) of $C_{5+}$ olefins. Additionally or alternately, the recycle stream can include 20 wt % or more of $C_{6+}$ olefins relative to a weight of the recycle stream, or 40 wt % or more, or 60 wt % or more, such as up to being substantially entirely composed of $C_{6+}$ olefins.

Using naphtha boiling range compounds from the effluent as a recycle portion and/or naphtha boiling range alkanes as a co-feed can provide a variety of advantages. Any olefins in the recycle portion can undergo additional oligomerization, thus increasing the yield of distillate. The alkanes in the recycle portion can serve as an additional diluent. This can assist with managing the temperature increase in the reactor(s). Additionally, it has been discovered that mixing naphtha boiling range olefins with the olefin-containing feed provides an unexpected increase in cetane rating when operating under adiabatic conditions, as compared with mixing just naphtha boiling range alkanes with the olefin-containing feed. The molar ratio of olefins in the recycle stream relative to olefins in the fresh feed can range from 0.5 to 2.0 (i.e., 0.5 to 2.0 moles olefins in recycle stream per 1.0 moles olefin in fresh feed), or 0.5 to 1.0, or 0.7 to 2.0, or 0.7 to 1.0.

It is noted that the olefins in the recycle portion can assist with managing the temperature in the reactors. Although the olefins in the recycle portion can also oligomerize, the excess heat generated from oligomerization of a larger olefin is less than the excess heat generated from oligomerization of a smaller olefin. For example, two potential oligomerization reactions can be considered where propylene ($C_3$ olefin) is reacted with either a $C_4$ olefin or a $C_8$ olefin to form a larger olefin. The enthalpy of reaction for reacting the $C_3$ olefin with the $C_4$ olefin is roughly 10 kJ/mol larger than the enthalpy of reaction with the $C_8$ olefin. This is shown in Equations (1) and (2), where "$C_x=$" corresponds to an olefin containing "x" carbon atoms.

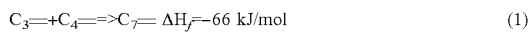

$$C_3= + C_4= => C_7= \quad \Delta H_f = -66 \text{ kJ/mol} \quad (1)$$

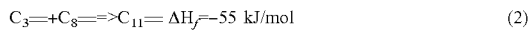

$$C_3= + C_8= => C_{11}= \quad \Delta H_f = -55 \text{ kJ/mol} \quad (2)$$

After the oligomerization reaction, the oligomerized effluent can include unreacted feed, naphtha boiling range compounds, and distillate boiling range compounds. It is noted that oligomerization typically corresponds to combining two olefins to form a larger olefin. Thus, the oligomerization effluent can include a substantial content of olefins. Prior to using the distillate boiling range compounds as a fuel, the distillate boiling range compound can be exposed to an olefin saturation process or another type of hydrotreating.

Another advantage of using moving bed 3-phase reactor with recycle is that desirable yields of distillate can be achieved. Depending on the aspect, the yield (wt %) of distillate relative to the wt % of olefins in the fresh feed can be from 20 wt % to 80 wt %. Additionally, as noted above, recycling of heavy olefins ($C_5+$) from the effluent can provide an unexpected increase in cetane for the resulting hydrotreated distillate.

Reaction Conditions and Catalyst

Olefin oligomerization conditions can include one or more of: a reactor inlet temperature of 120° C. to 182° C. (~250° F. to ~360° F.), or 138° C. to 160° C. (~280° F. to ~320° F.); a reactor outlet temperature of 200° C. to 220° C. (~390° F. to ~430° F.); an average reactor temperature of 170° C. to 190° C.; a fresh feed olefin partial pressure of 200 psig to 300 psig (~1.4 MPa-g to ~2.1 MPa-g), or 200 psig to 240 psig (~1.4 MPa-g to 1.7 MPa-g); and a fresh olefin feed rate corresponding to a weight hourly space velocity (WHSV) of 0.1 $hr^{-1}$ to 10 $hr^{-1}$, or 0.5 $hr^{-1}$ to 2.0 $hr^{-1}$, or 1.0 $hr^{-1}$ to 1.5 $hr^{-1}$. In this discussion, average reaction temperature is defined as the average of the temperature at the reactor inlet and the temperature at the reactor outlet for the reactor where the conversion reaction is performed. In some aspects, the reaction conditions between reactors within a series of reactors can be substantially the same. In some aspects, the reaction conditions can vary between reactors within a series of reactors, depending on the reaction taking place in each moving bed reactor.

In various aspects, a zeolite catalyst composition can be used for olefin oligomerization. In this discussion and the claims below, a zeolite is defined to refer to a crystalline material having a porous framework structure built from tetrahedra atoms connected by bridging oxygen atoms. Examples of known zeolite frameworks are given in the "Atlas of Zeolite Frameworks" published on behalf of the Structure Commission of the International Zeolite Association", $6^{th}$ revised edition, Ch. Baerlocher, L. B. McCusker, D. H. Olson, eds., Elsevier, New York (2007) and the corresponding web site, http://www.iza-structure.org/databases/. Under this definition, a zeolite can refer to aluminosilicates having a zeolitic framework type as well as crystalline structures containing oxides of heteroatoms different from silicon and aluminum. Such heteroatoms can include any heteroatom generally known to be suitable for inclusion in a zeolitic framework, such as gallium, boron, germanium, phosphorus, zinc, and/or other transition metals that can substitute for silicon and/or aluminum in a zeolitic framework.

A suitable zeolite can include a 1-dimensional 10-member ring pore channel network. Examples of suitable zeolites having a 1-dimensional 10-member ring pore channel network include zeolites having a MRE (e.g, ZSM-48), MTW, TON (e.g., ZSM-22), MTT (e.g., ZSM-23), and/or MFS framework. In some aspects, ZSM-48, ZSM-22, MCM-22, MCM-49, or a combination thereof can correspond to preferred zeolites.

Generally, a zeolite having desired activity for olefin oligomerization can have a silicon to aluminum molar ratio of 5 to 200, or 15 to 100, or 20 to 80, or 20 to 40. For example, the silicon to aluminum ratio can be at least 10, or at least 20, or at least 30, or at least 40, or at least 50, or at least 60. Additionally or alternately, the silicon to aluminum ratio can be 300 or less, or 200 or less, or 100 or less, or 80 or less, or 60 or less, or 50 or less.

It is noted that the molar ratio described herein is a ratio of silicon to aluminum. If a corresponding ratio of silica to alumina were described, the corresponding ratio of silica (Sift) to alumina ($Al_2O_3$) would be twice as large, due to the presence of two aluminum atoms in each alumina stoichiometric unit. Thus, a silicon to aluminum ratio of 10 corresponds to a silica to alumina ratio of 20.

In some aspects, a zeolite in a catalyst can be present at least partly in the hydrogen form. Depending on the conditions used to synthesize the zeolite, this may correspond to converting the zeolite from, for example, the sodium form. This can readily be achieved, for example, by ion exchange to convert the zeolite to the ammonium form followed by calcination in air or an inert atmosphere at a temperature of 400° C. to 700° C. to convert the ammonium form to the active hydrogen form.

A catalyst composition can employ a zeolite in its original crystalline form or after formulation into catalyst particles, such as by extrusion. A process for producing zeolite extrudates in the absence of a binder is disclosed in, for example, U.S. Pat. No. 4,582,815, the entire contents of which are incorporated herein by reference. Optionally, such an "unbound" catalyst can be steamed after extrusion. The terms "unbound" is intended to mean that the present catalyst composition is free of any of the inorganic oxide binders, such as alumina or silica, frequently combined with zeolite catalysts to enhance their physical properties.

The catalyst compositions described herein can further be characterized based on activity for hexane cracking, or Alpha value. Alpha value is a measure of the acid activity of a zeolite catalyst as compared with a standard silica-alumina catalyst. The alpha test is described in U.S. Pat. No. 3,354, 078; in the Journal of Catalysis, Vol. 4, p. 527 (1965); Vol.

6, p. 278 (1966); and Vol. 61, p. 395 (1980), each incorporated herein by reference as to that description. The experimental conditions of the test used herein include a constant temperature of 538° C. and a variable flow rate as described in detail in the Journal of Catalysis, Vol. 61, p. 395. Higher alpha values correspond with a more active cracking catalyst. For an olefin oligomerization catalyst, Alpha value can be 15 to 150, or 15 to 100, or 15 to 50.

As an alternative to forming catalysts without a separate binder, zeolite crystals can be combined with a binder to form bound catalysts. Suitable binders for zeolite-based catalysts can include various inorganic oxides, such as silica, alumina, zirconia, titania, silica-alumina, cerium oxide, magnesium oxide, yttrium oxide, or combinations thereof. For catalysts including a binder, the catalyst can comprise at least 10 wt % zeolite, or at least 30 wt %, or at least 50 wt %, such as up to 90 wt % or more. Generally, a binder can be present in an amount between 1 wt % and 90 wt %, for example between 5 wt % and 40 wt % of a catalyst composition. In some aspects, the catalyst can include at least 5 wt % binder, such as at least 10 wt %, or at least 20 wt %. Additionally or alternately, the catalyst can include 90 wt % or less of binder, such as 50 wt % or less, or 40 wt % or less, or 35 wt % or less. Combining the zeolite and the binder can generally be achieved, for example, by mulling an aqueous mixture of the zeolite and binder and then extruding the mixture into catalyst pellets. A process for producing zeolite extrudates using a silica binder is disclosed in, for example, U.S. Pat. No. 4,582,815. Optionally, a bound catalyst can be steamed after extrusion.

Moving Bed Reactors for Olefin Oligomerization

In various aspects, one or more moving bed reactors, such as a plurality of moving bed reactors arranged in series, can be used to oligomerize olefins to form distillate boiling range compounds. Using moving bed reactors for olefin oligomerization can provide a variety of advantages. For example, moving bed reactors can allow for control of the residence time of catalyst particles within the reactors prior to regeneration. In combination with selecting a desired level of coke removal during regeneration, the residence time in the moving bed reactors can allow for control over the average amount of coke on catalyst within the reactor. By controlling the coke level on catalyst, the activity of the catalyst for the oligomerization reaction can be maintained at a desired level. Maintaining a desired level of coke can also reduce or minimize fouling and/or clogging of the moving bed reactors.

The amount of coke on the catalyst in the reactor can be characterized in various ways. One option can be to characterize the average amount of coke on catalyst that is delivered from the regenerator to the first reactor. For catalyst that is not fresh catalyst, this corresponds to the minimum coke level on the catalyst. In some aspects, the amount of coke on regenerated catalyst can correspond to 0.1 wt % to 5.0 wt % of the weight of the catalyst, or 0.5 wt % to 2.5 wt %, or 1.0 wt % to 5.0 wt %, or 1.0 wt % to 2.5 wt %. In other aspects, substantially complete regeneration of catalyst can be performed, so that the amount of coke on catalyst after regeneration is less than 1.0 wt %, or less than 0.1 wt %.

As another example, using a moving bed reactor avoids the problem in fixed bed reactors where the entire catalyst volume is exposed to any steam that is present in the reaction environment. Instead, only catalyst currently within the moving bed reactors is exposed to water within the reaction environment. This can reduce or minimize reductions in catalyst activity due to steaming.

At the reaction temperatures for olefin oligomerization, the olefin-containing feed can typically correspond to a gas phase feed. However, the naphtha boiling range portions of the recycle stream can include liquid phase components. Additionally, as oligomerization occurs, distillate boiling range components are formed that will be in the liquid state under the reaction conditions. As a result, performing olefin oligomerization for formation of distillate compounds can result in three phases being present within the reactors.

In various aspects, a plurality of moving bed reactors, arranged for serial processing, can be used for upgrading of olefins to form distillate boiling range compounds. The plurality of reactors can be any convenient number that allows conversion of the feed to reach a desired level of completion. In some aspects, the number of reactors can be selected to achieve a desired level of oligomerization (such as a desired yield of distillate boiling range compounds) for the olefins in the olefin-containing feed.

Some considerations for selection of reactor size and number of reactors can be related to managing the temperature gradient across each reactor. Preferably, the temperature gradient across a single reactor can be 85° C. or less (~150° F. or less), or 70° C. or less, or 50° C. or less, or 40° C. or less. Due in part to higher feed concentration of smaller olefins at the beginning of a series of reactors, if a series of reactors includes equal amounts of catalyst (i.e., reactors of equal size), the temperature gradient across the first reactor in the series, and then decrease across each successive reactor. For example, for three reactors in series, the temperature gradient across the first reactor would be larger than the temperature gradient across the second reactor, while the second reactor temperature gradient would be larger than the third reactor temperature gradient. In order to account for this, the size/amount of catalyst for reactors later in the series can be larger than reactors earlier in the series. This can increase the time of catalyst exposure to feed in the later reactors. In some aspects, this can be used to allow two or more reactors in series to have a similar temperature gradient, such as up to all reactors in a series. In other aspects, the first reactor in a series can have a different, smaller size/smaller amount of catalyst than at least one other reactor in the series, with each reactor in the series being at least as large/containing at least as much catalyst as the prior reactor. Still other potential methods for selecting reactor size/catalyst amount can also be used. It is noted that catalyst amount refers to the amount of catalyst used during operation of a moving bed reactor. Thus, in configurations where a separate catalyst flow controller is used after each reactor, it can be possible to have moving bed reactors with different amounts of catalyst even though the volume for holding catalyst in each reactor is similar.

In some aspects, the second reactor can contain an equal or greater amount of catalyst than the first reactor. In such aspects, the weight ratio of catalyst in the first reactor relative to the second reactor can be between 1:4 and 1:1, or between 1:3 and 1:1.

With regard to managing temperature, during or after removal of catalyst and fluids from a reactor, one or more steps can be taken to reduce the temperature in the next reactor. For example, the stripping gas used to disengage fluids from the catalyst can also serve as a quench gas. This can allow the inlet temperature two or more reactors in a series, such as up to each reactor in a series, to be substantially similar. Reactors can be considered to have substantially similar inlet temperatures if the average temperature of catalyst and fluid entering the reactor is within 10° C. The average temperature of catalyst and fluids entering a reactor can correspond to a weighted average based on the weight of each component entering the reactor during a unit time.

In some aspects, an example of a suitable moving bed reactor for performing oligomerization of olefins in a multistage moving bed reactor system can include a feed distribution apparatus for introducing a 3-phase flow under co-current flow conditions. The feed distribution apparatus can allow for separate introduction of liquid and solids in a manner that allows for even distribution of liquid within the solids. The gas portion of the flow can be introduced in any of a variety of convenient manners for distributing gas into a liquid or solid flow.

The distribution apparatus allows for efficient and/or substantially even distribution of a co-current axial liquid flow in a solid particle flow based on the relative angle of introduction for the liquid and the solid particles. The solid particles can be introduced into the reactor by allowing the particles to drop under gravitational pull. The conduit dropping the particles can also be narrower than the portion of the reactor that is receiving the particles. This can result in the solid particles forming a cone based on the angle of repose for the solid particles. The liquid can then be introduced at a plurality of locations around the cone. The distribution channels for introducing the liquid can be angled at the exit point, so that the liquid has a lateral velocity component. Introducing the liquid with a lateral velocity component can facilitate mixing of the liquid with the solid particles. However, even though the liquid initially has a lateral velocity component, at least a majority of the liquid travels axially with the catalyst through substantially the full length of the reactor prior to disengagement of the majority of the liquid from the solids. Any gas in a three-phase flow can be contacted with the solid and liquid in an axial flow manner, a radial flow manner, or in any other convenient manner that allows for a desired distribution pattern.

Because the solid particles are being dropped into the reactor to allow formation of a cone, several options are available for controlling the rate of catalyst flow through the moving bed reactors. In some aspects, the flow rate of catalyst particles through a moving bed reactor can be controlled using a catalyst flow controller valve at the bottom of the reactor. This type of control over the catalyst flow through a moving bed reactor can be used in any convenient configuration one or more moving bed reactors. Using a catalyst flow controller valve at the bottom of a reactor can also limit the flow of catalyst delivered to the next moving bed reactor. Limiting the catalyst flow rate into a reactor can ensure that sufficient space is available in the reactor volume for the desired cone to form at the angle of repose. In addition to the catalyst flow controllers at the bottom of each reactor, a catalyst flow controller can also be included between the catalyst source and the first reactor in a series of reactors. For example, a flow controller can be placed at the exit of a catalyst regenerator that is used to provide regenerated catalyst to the first reactor in a series of reactors. An example of a suitable flow controller is described in U.S. Pat. No. 10,188,998.

In other aspects where a plurality of moving bed reactors are arranged as a vertical stack, the flow rate to all of the reactors in the vertical stack can be controlled using a catalyst flow controller, plus the geometry of the transfer conduit(s) between reactors. In this type of configuration, a substantial portion of the flow rate control can be dependent on gravity-assisted flow control. The flow controller can be located at the bottom of the final reactor in the vertical stack. This can control the overall flow of catalyst through the series of reactors. The geometry of the conduits between the reactors can then be used to control the flow rate of catalyst between reactors. In particular, the conduit size between reactors can narrow to restrict flow of catalyst between reactors. This can allow sufficient head space to be available at the top of each catalyst bed so that a cone of catalyst can form at the angle of repose.

It is noted that the distributor apparatus can work in conjunction with methods for separating a three-phase flow as the flow exits from the moving bed reactor. By separating the three-phase flow into gas, liquid, and solid components, the components can be re-combined in a subsequent moving bed stage using the distributor apparatus. The separation of the fluid phases from the catalyst flow can be effective for separating 95 wt. % or more of the hydrocarbons in the oligomerization effluent from the catalyst flow.

One example of a suitable method for separating the three-phase flow into gas, liquid, and solid components can be to use a stripping gas in combination with concentric pipes to allow for separate capture of the gas and liquid. For example, the stripping gas can be passed through the solid particles at a location prior to the solids exit conduit. This can cause any liquids and gases entrained with the solid particles to be driven out of the volume containing the solids and into a separate volume, such as an outer pipe of a pair of concentric pipes. The wall between the inner pipe and the outer pipe can include protected openings, such as bubble caps, that allow transport of gas from the outer pipe to the inner pipe while minimizing transport of liquids. The liquids can instead accumulate at the bottom of the outer pipe and exit from openings that can be accessed when the accumulated liquid level is sufficiently high. U.S. Patent Application Publication 2017/0137342 shows an example of this type of structure.

Configuration Example 1—Olefin Oligomerization

Figure 6:
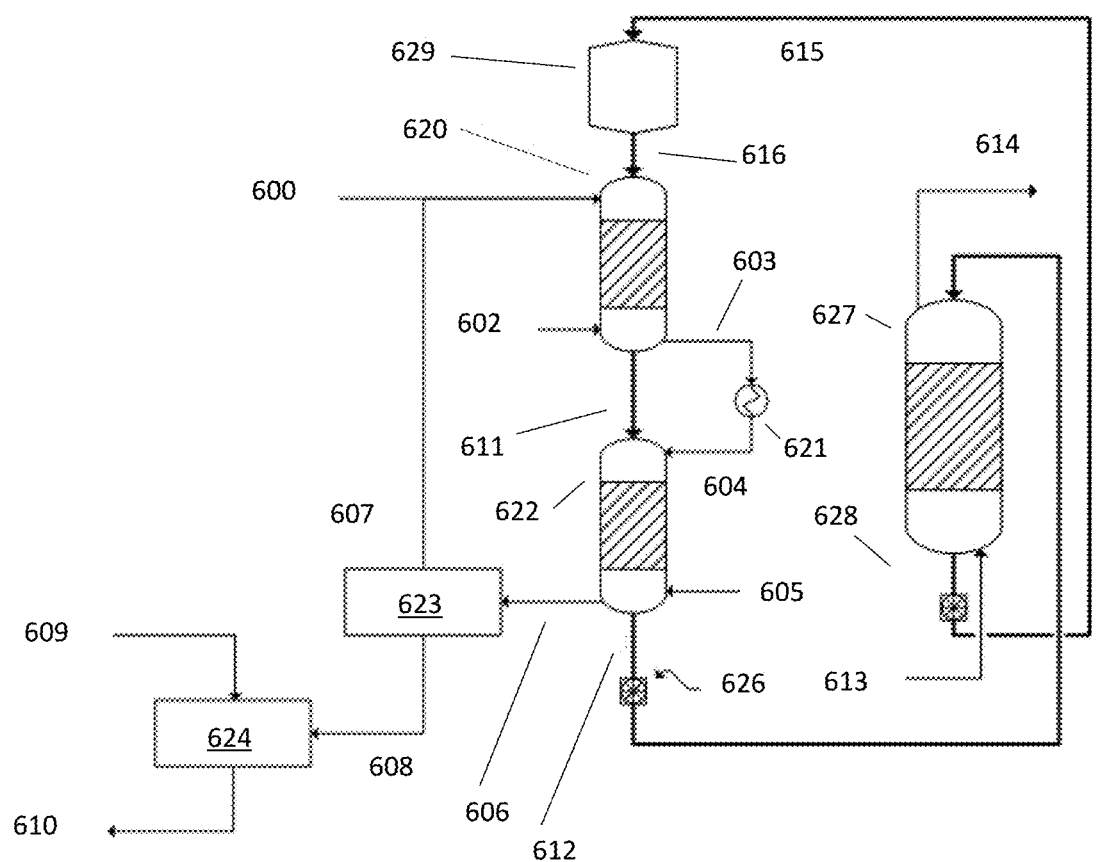
FIG. 6 shows an example of a reactor configuration for conversion of olefins to distillate boiling range compounds.

FIG. 6 shows an example of a process configuration for using multiple moving bed reactors to oligomerize olefins to distillate compounds. In FIG. 6, the reactor is 2-stage vertically stacked moving bed reactor operating in adiabatic mode. Fresh catalyst enters from the top of the first stage reactor and is removed from the bottom of the second stage reactor. The catalyst movement is gravity-assisted and is controlled using a catalyst flow controller valve. Fresh feed 600 is an olefin-containing feed, preferably containing 70 wt % or more of $C_3$-$C_5$ olefins relative to a weight of olefins in the feed.

The fresh feed 600 reacts with the 1-D, 10-member ring catalyst beads in the reactor and the exothermic oligomerization reaction begins. ZSM-48 is an example of a suitable catalyst for forming the catalyst beads. As the reaction progresses, the molecular weight of the oligomerized hydrocarbon products increases as well beyond a certain molecular weight and under the reaction conditions the products start changing phase and liquid phase begins to appear. The reactor operates adiabatically and at the bottom of the first stage reactor 620 the unreacted feed and products are separated from the catalyst bed in a separation chamber. In the configuration shown in FIG. 6, the unreacted feed and products are separated using a stripping gas 602. In other aspects, the separation can be performed by any convenient method. For example, if the oligomerization reaction has not resulted in liquid olefins by the end of the first stage, the first stage effluent can be performed as a gas-solid separation. Such a separation can be achieved, for example, using downcomers to generate an appropriate pressure balance so that the gas exits via effluent line 603. The separation chamber is designed to efficiently separate the gas/liquid phase from the solid phase (catalyst). The stripping gas can be inert such as steam or nitrogen, or can be the reactants for stage feed injections, or a combination thereof. The stripping gas pushes the unreacted feed and products into the effluent line 603 to be cooled in heat exchanger 621 and returns to the top of the second stage reactor 622 via line 604.

The oligomerization reaction continues in the second stage 622. Feed olefin conversion in the reactor is greater than 95% and the product, which is mostly olefin, is all liquid phase. A stripping gas 605 is used to remove the products from 622 and send it to a fractionation unit 623 via line 606. The fractionation unit operates at 330° F. (~165° C.) cut point. The lighter species having boiling points lower than 165° C. and considered to be in the gasoline range hydrocarbons are recycled back to the first stage reactor via line 607 as a liquid stream. The bottom of the fractionation unit 623 which is the olefin diesel range products is sent to a reactor 624 to hydrogenate the olefin feed to paraffin using $H_2$ 609.

As the oligomerization reaction progress in the reactor coke is deposited on the catalyst particles and the catalyst activity drops over time. In order to maintain a stable yield and catalyst activity, the catalyst is slowly moved from top to bottom via gravity. The catalyst flow speed is controlled at the bottom of the last reactor stage 622 using a catalyst roller 626. The speed of catalyst flow is based on the rate of catalyst deactivation which could range anywhere between 1-30 days, or between 15-20 days. At steady state there can be an axial coke distribution profile along the reactor. Catalyst flows from first to second stage via transfer line 611 and is removed from the bottom of second stage via line 612 to be sent to a regenerator 627. Line 612 could move the catalyst using different techniques including but not limited to pneumatic pressure, conveyer belt, a screw feeder, or another convenient method. In the regenerator air 613 is introduced to burn the coke off the catalyst particle. The flue gas is vented through 614. The catalyst flow out of the regenerator is controlled using a catalyst roller 628. The regenerated catalyst is sent via line 615 pneumatically or conveyed or by other technique to a catalyst hopper 629 which controls the catalyst feed to the reactor via line 616. The size of the catalyst hopper will depend on the rate difference between the catalyst in the reactor and the regenerator.

Configuration Example 2—Example of Distributor Apparatus

In various aspects, oligomerization of olefins to distillates in moving bed reactors can be performed using reactors that can provide relatively uniform distribution of liquid in the catalyst particles within a moving bed reactor. One option for achieving a relatively uniform distribution is to use a distributor apparatus that can allow uniform distribution of liquid in the catalyst particles under co-current axial flow conditions for the solids and liquids. When using such a distributor apparatus, the vapor flow in the moving bed reactors can correspond to radial flow or axial flow.

FIG. 1 shows an example configuration for a distributor apparatus for a moving bed reactor. The distributor apparatus can be used for moving bed reactors where solids and liquids substantially travel through the reactor as an axial flow, while the gas flow can correspond to an axial flow, a radial flow, or any other convenient flow pattern. In some aspects, the distributor apparatus shown in FIG. 1 can be used in conjunction with a moving bed reactor where the catalyst is introduced along the central axis of the reactor. This can result in the catalyst filling a central volume of the reactor. Such a configuration for a moving bed reactor can be suitable, for example, for a moving bed reactor where the catalyst, liquid, and gas all substantially traverse the reactor as axial flows. In other aspects, multiple instances of the distributor apparatus in FIG. 1 can be arranged to provide catalyst for an annular catalyst volume in a moving bed reactor. This can be beneficial for configurations such as the example shown in FIG. 4, where the catalyst and liquid in the moving bed reactor travel in a substantially axial direction, while the gas in the feed contacts the catalyst as a radial flow.

FIG. 1 shows a side view of an example of a distributor apparatus for distribution of liquid when the solids are introduced along a central axis. In FIG. 1, a liquid distributor plate 101 is shown and highlighted with hatch lines. The liquid distributor plate 101 fits into a moving bed reactor system through a system of connecting parts at the top and bottom of the distributor plate 101. The inlet feed pipes 102 are attached on the side of the top connecting part 103. Depending on the configuration, inlet feed pipes 102 can transport feed into the reactor in the form of gas, liquid, or a combination of gas and liquid. For example, in aspects where the gas portion of a feed contacts the catalyst as a substantially radial flow, inlet feed pipes 102 can transport a liquid portion of the feed into the reactor, with substantially all of the gas entering the reactor as a separate flow.

Figure 2:
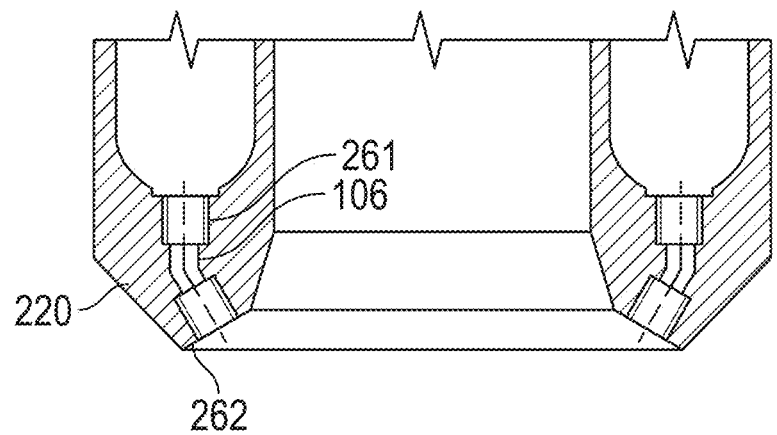
FIG. 2 shows additional details for portions of the feed distribution apparatus in FIG. 1.

In FIG. 1, the catalyst particles enter the vessel through a solids inlet conduit, such as catalyst feed line 104, which is attached in the center of the top connecting part 103. The distributor plate 101 sits below the top connecting part 103. The portion of the feed provided by inlet pipes 102 drops into the distributor plate which includes one or more concave shapes 105 with a radius R (shown in FIG. 2). There are a number of slots (or orifices) 106 placed around the distributor plate. Preferably, the slots can be placed evenly and concentrically around the distributor plate. The slots provide fluid communication between the concave shape(s) 105 and a solids volume 108. As shown in FIG. 2, these slots have a depth at the top 261 of the slots 106 and a depth at the bottom 262 of the slots 106. The slots can optionally be threaded on both ends (i.e., at top 261 and at bottom 262) to allow installation of nozzles at both the top and the bottom (not shown). The nozzles can correspond to, for example, hollow cylinders with an opening at the top to allow the passage of the gas. In some aspects, the nozzles can further include a slit around the top side of the nozzle. This can allow liquid to flow through once a certain liquid height is built. This will prevent selective distribution of the liquid through certain nozzles and allow an even flow of the liquid through all the nozzles. It is noted that the nozzles at the bottom 262 of the slots 106 can have a geometry that is selected to facilitate distribution of the expected type of feed that is passing through the slots 106, such as nozzles selected for distribution of gas, liquid, or a mixture of gas and liquid.

Figure 4:
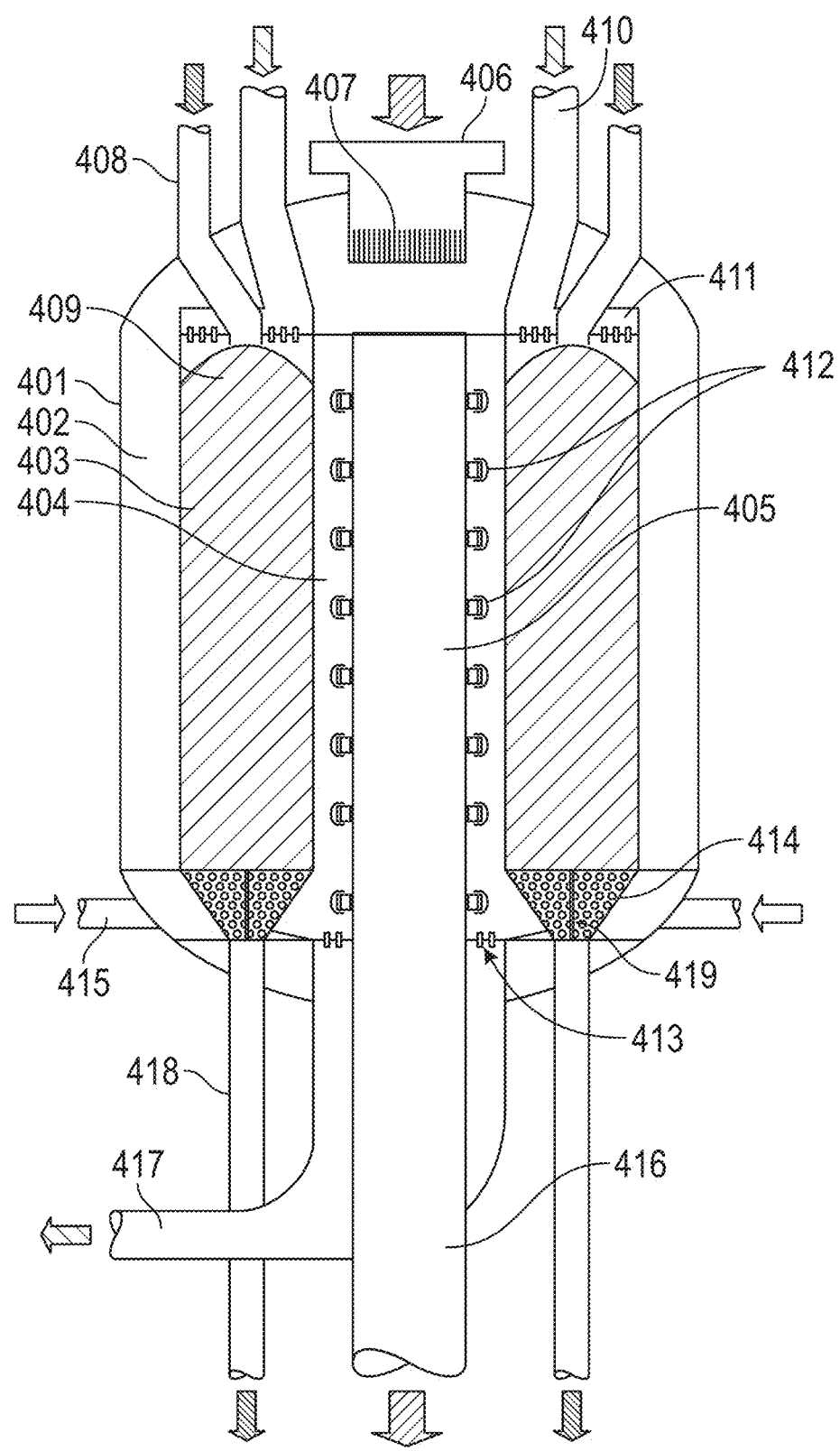
FIG. 4 shows a side view an example of a moving bed reactor.

Depending on the aspect, solids volume 108 can correspond to a single central volume, an annular volume, or another convenient volume that allows for axial flow of catalyst and liquid through a moving bed reactor. In aspects where solids volume 108 corresponds to a central volume in a reactor, a single solids inlet conduit 104 can provide catalyst to the solids volume 108. As another example, in aspects where solids volume 108 corresponds to an annular volume, a plurality of distributor apparatus can be arranged in a substantially symmetric manner around the solids volume 108. Such a configuration is shown in FIG. 4. It is noted that in a radial gas flow configuration, the wall defining solids volume 108 can be perforated and/or porous to allow gas to contact the liquid and solid that are flowing axially down through the reactor.

In the example of a distributor apparatus shown in FIGS. 1 and 2, the bottom of the distributor plate 101 curves toward the inside of the solids volume at a 45 degree angle (or more generally an angle between 30° and 55°). The gas and/or liquid will enter the nozzles inserted into the distributor plate's slots (or orifices) 106 and first drop a distance prior to then curving inward, such as at a 60 degree angle as shown in FIG. 2 (or more generally an angle between 45° and 70°). The gas and/or liquid can then travel a further distance to exit through another (bottom) set of nozzles inserted into slots 106, as shown in FIG. 2. As shown in FIG. 1, the distributor plate sits on top of the bottom connecting part 107 which has a form of a funnel whose bottom diameter is that of the solids volume 108 and top diameter is that of the distributor plate. The top connecting part 103, the distributor plate 101, and the bottom connecting part 107 are held together with a bolted clamp 109. The bottom connecting part 107 can either be welded to the top of the reactor vessel 108, as shown in FIG. 1, or bolted with a flange (not shown).

At the interface 120 between catalyst feed line (or other solids inlet conduit) 104 and solids volume 108, a characteristic width of the catalyst feed line 104 can be smaller than a characteristic width of the solids volume that is receiving the catalyst. The characteristic width of the catalyst feed line 104 corresponds to the longest straight line that can be drawn between two points on the catalyst feed line at the interface 120 with the solids volume 108. In aspects when the catalyst feed line is roughly cylindrical, the characteristic width will be the diameter of the catalyst feed line. The width of the solids volume receiving the catalyst particles can correspond to a) for a central volume, the diameter of a cylindrical volume as measured at the location where the base of the catalyst cone forms in the reactor; b) for an annular volume, the radial distance between the outer surface and the inner surface that define the annular volume, at the location where the base of the catalyst cone forms in the annular volume; or c) a similarly characteristic width for a volume having a shape other than an annular volume or a cylindrical volume.

It is noted that the above definitions for the width of the solids volume are based on the location of where the base of the catalyst cone forms. Above the base of the cone, there can typically be a gap between the interface of the catalyst feed line with the solids volume and the base of the catalyst cone. This gap, which can be referred to as a contact zone or mixing zone, corresponding to the difference between the top of the solids volume and the top of the reaction zone volume, allows the catalyst cone to form at the angle of repose.

During operation, the solid (catalyst) particles exit the catalyst feed line 104 and distribute inside the solids volume 108, forming a conical shape 110 whose angle corresponds to the angle of repose of the solid particles. The conical shape 110 is formed in part because the characteristic width of the solids inlet conduit(s) is smaller than the width of the volume receiving the solid particles. The angle of repose for solid particles can vary, such as having an angle of repose of roughly 10° to 40°. The bottom inner edge of the feed distributor plate where it meets the catalyst feed line bottom can be slightly angled, such as having an angle from 10° to 25°. The gas or gas/liquid exiting the distributor plate through an exit surface via the bottom nozzles of slots 106, can inject directly on top of the cone of particles (at the angle of repose) formed by the flow of solid particles into the reactor. This will allow enhanced fluid mixing from the top and let the fluid evenly disperse radially as it flows downward. This is due in part to the lateral velocity of the feed toward the central axis, which can assist with having feed well-mixed with particles throughout the reaction zone volume.

Figure 3:
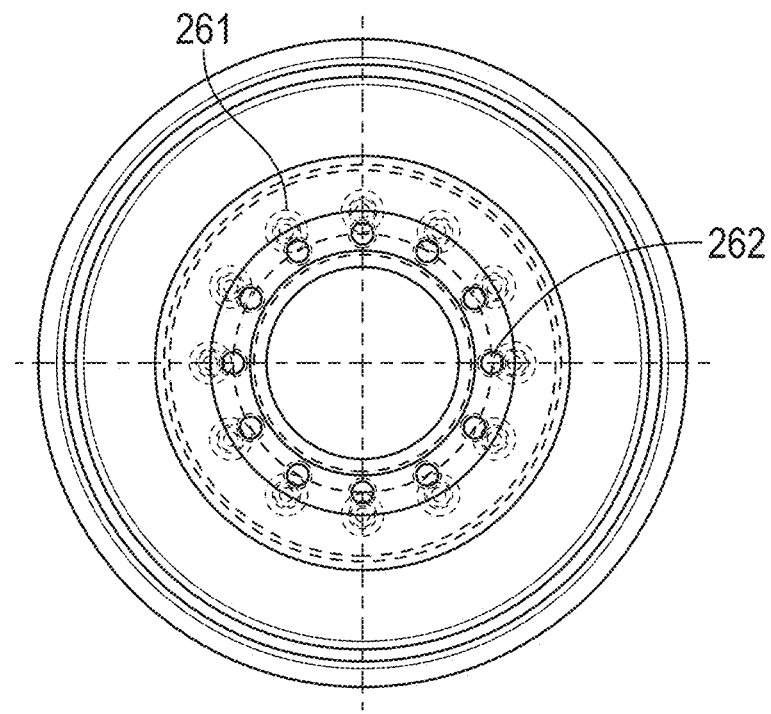
FIG. 3 shows a bottom view of the feed distribution apparatus shown in FIG. 1.

FIG. 3 shows the bottom of the distributor plate. In this schematic there are 12 orifice nozzles at the top 261 and bottom 262. The offset between the center of the top and bottom nozzles as the distributor plate curves inward toward the center of the reactor vessel can also be seen in this figure. In various aspects, the number of the nozzles can be determined based on the scale of the reactor vessel, the optimum distance needed to space the nozzles, and the liquid mass flux.

It is noted that the above description contemplates having a distributor apparatus that is machined as a separate part from other parts of the overall reaction system. In other aspects, the distributor apparatus can be integrated with the overall reaction system in any convenient manner. For example, the distribution plate can be attached to the catalyst feed line (or other solids inlet conduit) 104, so that there is no visible joint between catalyst feed line 104 and the distributor plate. In such an aspect, the "opening" in the distributor plate that allows catalyst to pass from feed line (or other solids inlet conduit) 104 to the solids volume 108 can correspond to a part of the solids inlet conduit 104. It is noted that the attachment between catalyst feed line 104 and the distributor plate can correspond to a removable attachment, or that attachment can correspond to the catalyst feed line 104 and the distributor plate corresponding to a single piece. Alternatively, the distributor apparatus and catalyst feed line 104 can be separate pieces, with the catalyst feed line 104 passing through an opening in the distributor apparatus.

Configuration Example 5—Reactor with Annular Catalyst Volume (Radial Gas Flow)

FIG. 4 shows an example of a moving bed reactor suitable for performing a co-current reaction in the presence of three phases. The reactor in FIG. 4 is designed to introduce the catalyst and liquid into an annular volume. The solid and liquid can flow axially through the annular volume. The gas phase portion of the feed can then be passed through the catalyst and liquid in a substantially radial direction.

In FIG. 4, reaction vessel 401 includes an outer annular volume 402 and an inner annular volume 403. The inner annular volume 403 is the annular region where the catalyst or other solid particles reside, and therefore can be referred to as an annular solids volume. The outer annular volume 402 and inner annular volume 403 are arranged around a central double pipe or conduit, corresponding to an outer central pipe or conduit 404 and an inner central pipe or conduit 405. The inner annular volume 403 can include perforations (not shown) that permit vapor communication between the inner annular volume 403 and outer central pipe 404. The perforations can primarily allow gas to pass into the outer central pipe 404, but some liquid can also pass through the perforations. The perforations are small enough to retain substantially all of the solid particles in the annular solids volume 403. Similarly, perforations can be used to allow gas to pass between inner annular volume 403 and outer annular volume 402 while preventing transmission of solid particles.

During operation, gas is introduced into the reactor 401 via a central opening 406 which connects to an inlet pipe 407 with openings for distributing the gas into outer annular volume 402. The tops of inner annular volume 403, outer central pipe 404, and inner central pipe 405 are sealed at the top, so that the flow path for gas to reach the outer central pipe 404 is by passing radially through inner annular volume 403. During operation, solid particles (such as catalyst particles) are introduced into the reactor 401 via a plurality of pipes 408. The outlets of the plurality of pipes 408 are roughly centered over the mid-point of inner annular volume 403. Similar to the configuration shown in FIG. 1, the solid particles fall into the inner annular volume 403 and form cones 409 corresponding to the angle of repose for the particles. The liquid phase is passed into reactor 401 via a plurality of liquid conduits 410. The liquid conduits 410 feed a plurality of slots or openings 411 that are arranged around the pipes 408. Optionally, the slots or openings 411 can include nozzles. Also similar to FIG. 1, the slots or openings 411 are arranged to cause the liquid feed to impinge on the cones 409, in order to facilitate even distribution of liquid within annular volume 403. Optionally but preferably, the nozzles 411 can be oriented so that the liquid exiting from slots or openings 411 has a lateral velocity component. In some aspects, pipes 408 and liquid conduits 410 can have a similar relationship to inner annular volume 403 as the relationships between catalyst inlet flow 104, inlet pipes 102, and solids volume 108. In such aspects, liquid conduits 410 can be in fluid communication with annular volume 403 via the plurality of slots or openings 411, in a manner similar to how inlet pipes 102 are in fluid communication with solids volume 108 via slots or openings 106.

During operation, gas from outer annular volume 402 passes radially into inner annular volume 403. This allows contact between gas, liquid, and solid for performing a desired reaction. The gas then continues radially into the first or outer central pipe 404. Outer central pipe 404 includes a plurality of gas/liquid separation structures that can allow gas to pass through into inner central pipe 405 while retaining liquid entrained with the gas in outer central pipe 404. Example of these structures can include bubble caps, screen metal wire mesh, coalescing filter, and other suitable structures.

At the bottom of reactor 401, the gas, liquid, and solids can be separated to allow for further processing and/or or for introduction into a subsequent moving bed stage. The gas exits through a main gas exit line 416 that is in fluid communication with the bottom of inner central pipe 405. The solids can exit from inner annular volume 403 into a plurality of solids exit volumes, such as cone-shaped exit volumes 414 as shown in FIG. 4. A stripping gas 415 is passed through the solids exit volumes 414 to strip liquid from the solids prior to allowing the solids to exit via solids exit line 418. It is noted that a baffle 419 connects the cones 414 to the reactor wall 401, so that the stripping gas cannot bypass the cones. The stripping gas causes liquid in the solid particles to exit into the bottom of first or outer central pipe 404, where it is combined with any liquid collected by the bubble caps 412. The liquid can accumulate at the bottom of outer pipe 404 to a sufficient height so that the liquid can exit through openings 413 into liquid exit line 417. The liquid height is controlled using a control valve on line 417 (not shown).

Figure 5:
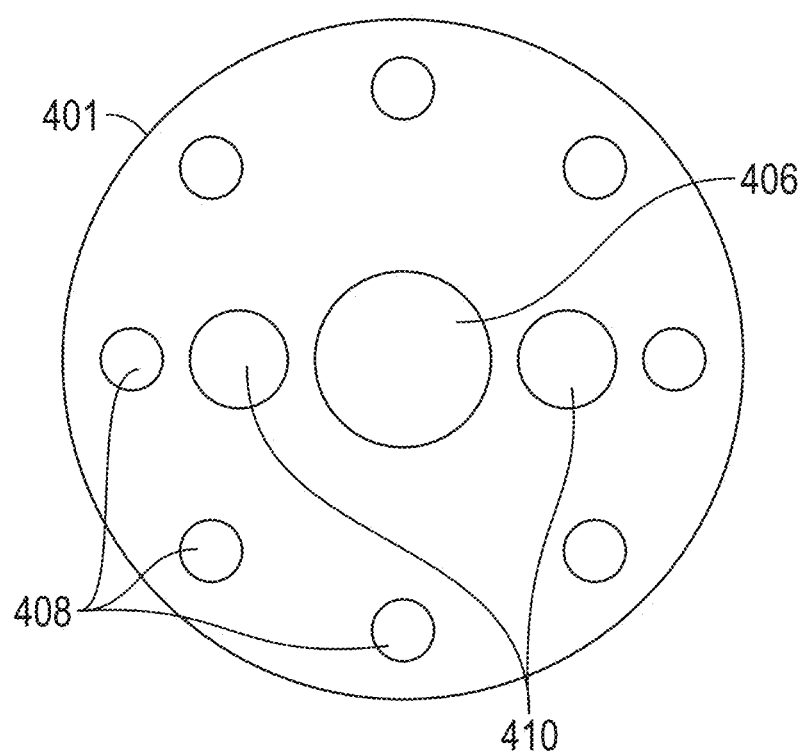
FIG. 5 shows a top view of the moving bed reactor shown in FIG. 4.

FIG. 5 shows a top view of the reactor 401 shown in FIG. 4. In FIG. 5, the input conduits corresponding to central opening 406, pipes 408 (for transfer of solid particles), and liquid conduits 410 are shown in relation to each other. It is noted that liquid conduits 410 are used within the reactor to provide liquid to a plurality of nozzles 411 (not visible in FIG. 5) that are arranged around each pipe 408.

It is noted that the configuration shown in FIG. 5 includes a total of 8 solids inlet conduits 408 and two liquid conduits 410. More generally, any convenient number of solids inlet conduits 408 and liquid conduits 410 can be used, so long as liquid is distributed around each solids inlet conduit. For example, in the configuration shown in FIG. 5, a distributor plate can be used to distribute the liquid feed from liquid conduits 410 around each of the solids inlet conduits 408. This can be performed by a single distributor plate that includes all of the liquid conduits 410 and solids inlet conduits 408. Alternatively, a part of distributor plates could be used, with each distributor plate receiving liquid from one liquid conduit 410 and distributing liquid to a portion of the solids inlet conduits 408. It is further noted that the annular solids volume could be segmented using one or more internal walls. This could allow a first group of solids inlet conduits 408 to provide catalyst particles to a first portion of the annular solids volume, while a second group of solids inlet conduits provides catalyst particles to a second portion of the annular solids volume. More generally, any convenient number of portions could be defined in the annular solids volume.

Example—Conversion of Olefins to Distillate

A first test (Run 1) was carried out to test the effect of liquid co-feed effect on the oligomerization reaction in a two-stage three-phase adiabatic moving bed reactor with a 50:50 wt. % catalyst distribution between the 2 stages using ZSM-48 catalyst. A mixture of $C_3=$ and $C_4=$ olefins were used as fresh feed and heptane was used as a liquid co-feed for heat management in the reactor. The weight ratio of heptane co-feed to fresh olefin-containing feed was roughly 1.4. The selection of heptane as non-reactive co-feed was made to study the extent of oligomerization reaction starting with light olefin feed. The olefin partial pressure in the total feed to the reactor was maintained at roughly 200 psig (1.4 MPa-g). Feed temperature was 350° F. (177° C.). In the first stage reactor the exotherm was kept below 430° F. (~220° C.). The WHSV of olefin was $0.5\ hr^{-1}$. The product from the reactor was sent to an offline fractionation unit and the products were fractionated at a 165° C. cut point. The 165° C.+ products were sent to a hydrogenation unit and the gasoline range olefin was used as co-feed for a subsequent test run. It should be noted that the fractionated gasoline stream also contains the initial heptane co-feed. The fraction of the heptane in the fractionated gasoline stream is about 73 wt %, meaning 27 wt % of the stream is olefinic gasoline range products. In a commercial embodiment the recycle would be substantially all olefin. A second test (Run 2) was then carried out with the same light olefin feed mixture of $C_3=$ and $C_4=$ with the same operating conditions as in Run 1, but using the stream containing 27 wt % of gasoline-range olefins as the co-feed.

Figure 7:
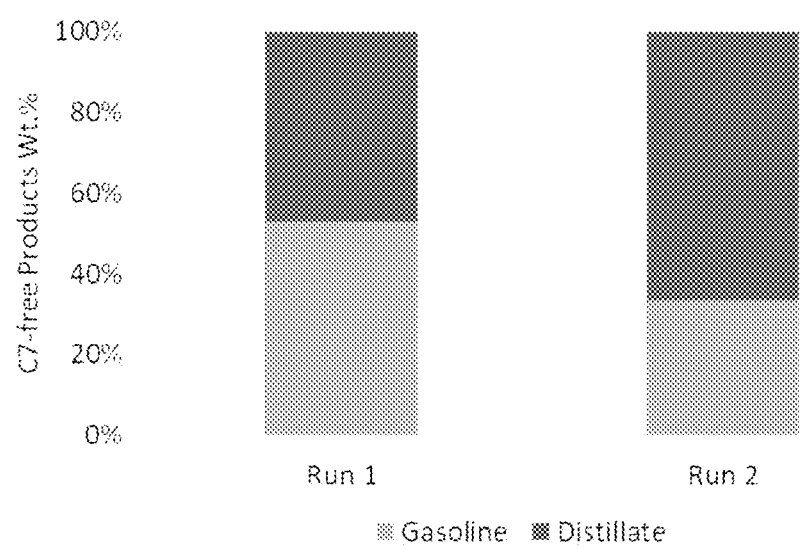
FIG. 7 shows product distributions from oligomerization of olefins.

FIG. 7 shows results from the two tests. The weight fraction of the product shown on the Y-axis is on a heptane-free basis. In this figure it can be seen that in Run 1 where heptane was used as co-feed the fraction between gasoline and diesel range products is about 53/47. In Run 2, however, it can be seen that the addition of the 27 wt % heavier olefin in the co-feed substantially increase the diesel range products so that the weight fraction between the gasoline and diesel becomes 33/67, confirming the additional benefit of heavier olefin recycle. Under commercial conditions this advantage may increase further as the olefin content in the recycle increases.

The diesel products from Run 1 and 2 from the moving bed test runs were hydrogenated with MAXSAT catalyst in a batch autoclave reactor system. The dried autoclave was loaded with 10 g of pre-dried catalyst in a basket. Then, 100-200 ml of the olefin diesel range product from the moving bed test runs was added to the autoclave. The autoclave was sealed up, purged and pressure tested with $N_2$ and $H_2$ respectively. After the successful pressure tests, the autoclave was heated to 150° C. with a stirring speed of 500 RPM. Once the reactor temperature reached 150° C., the pressure of the autoclave was re-adjusted to 600 psig (~4.1 MPa-g) and the reactor was kept running for 24 hrs. When the pressure declined below 3.4 MPa-g, the pressure was increased again to maintain 4.1 MPa-g during the run. The boiling range and composition of hydrogenated products were tested by 2D-GC. The tests confirmed the hydrogenated diesel range product with no visible olefin traces in 2D-GC spectra. A similar 2D-GC spectra of the olefin diesel range product showed that, prior to hydrogenation, the diesel range product was substantially composed of olefins with little or no paraffins.

The hydrogenated products were also characterized by simulated distillation according to ASTM D2887. The simulated distillation data show that more higher boiling range diesel molecules are produced by the addition of the 27 wt % heavier olefin in the co-feed. The change in boiling point profile of the products without (Run 1) and with (Run 2) olefins in the recycle stream is shown in Table 1.

TABLE 1

| Distillation of Diesel Boiling Range Products | | |
|---|---|---|
| Wt % off | Run 1 (° F.) | Run 2 (° F.) |
| 5% | 316 | 312 |
| 20% | 362 | 351 |
| 50% | 407 | 435 |
| 70% | 497 | 513 |
| 90% | 610 | 647 |
| 95% | 675 | 706 |
| 99.5% | 785 | 786 |

The hydrogenated products were further evaluated for properties related to diesel performance, including low temperature properties, oxidative stability and cetane number. The analytical test results are summarized in Table 2 below. The diesel product from the moving bed reactor exhibited an excellent cloud point of −58° F. and acceptable oxidation stability as measured by the oxidation induction time. The derived cetane numbers are excellent, exceeding the US limit at minimum 40 and EU limit at minimum 51.

When examining the cetane number as measured by NMR and the derived cetane number, it was found that the diesel produced by moving bed reactor in Run 1 had a similar NMR cetane value as the diesel generated by a fixed bed lab reactor operating isothermally (46.5 by NMR). However, the diesel product from Run 2 in the moving bed reactor provided an unexpected improvement in product cetane numbers over Run 1 as shown in Table 2. It is believed that this unexpected improvement would become greater as the olefin content in the recycle increases.

TABLE 2

| Distillate Fuel Properties | | |
|---|---|---|
| | Run 1 (° F.) | Run 2 (° F.) |
| Co-Feed | Heptane only | Heptane plus Olefin |
| Cloud Point (° F.) | <−58 | −58 |
| Time to pressure drop (min) | 50 | 42 |
| Ignition delay (ms) | 3.79 | 3.71 |
| Derived cetane number | 53.6 | 54.7 |
| NMR cetane test | 46.6 | 48.2 |

Additional Embodiments

Embodiment 1. A method for upgrading a feed to form distillate boiling range compounds, comprising: passing a catalyst flow comprising an olefin oligomerization catalyst into a first moving bed reactor of a plurality of serially connected moving bed reactors, the olefin oligomerization catalyst comprising a 1-D 10-member ring zeolite; exposing an olefin-containing feed comprising $C_3$-$C_8$ olefins and a recycle stream comprising at least 20 wt % $C_{5+}$ olefins to the catalyst flow in the plurality of moving bed reactors under olefin oligomerization conditions to form an oligomerized effluent, the olefin oligomerization conditions comprising substantially adiabatic operation of the plurality of moving bed reactors and an average reactor temperature of 170° C.-190° C.; separating the oligomerized effluent to form a distillate boiling range fraction and one or more lower boiling fractions, the one or more lower boiling fractions comprising the recycle stream.

Embodiment 2. The method of Embodiment 1, wherein the olefin oligomerization conditions comprise a temperature differential across a moving bed reactor of 85° C. or less.

Embodiment 3. The method of any of the above embodiments, wherein the olefin oligomerization catalyst comprises ZSM-48.

Embodiment 4. The method of any of the above embodiments, wherein the olefin-containing feed comprises 60 wt % or more of $C_3$-$C_5$ olefins relative to a weight of olefins in the olefin-containing feed.

Embodiment 5. The method of any of the above embodiments, wherein the olefin-containing feed comprises 5.0 wt % or less of $C_2$ olefins relative to a weight of olefins in the olefin-containing feed, or wherein the olefin-containing feed comprises 5.0 wt % or less of water relative to a weight of the olefin-containing feed, or a combination thereof.

Embodiment 6. The method of any of the above embodiments, wherein exposing the olefin-containing feed and the recycle stream to the catalyst flow comprises exposing the olefin-containing feed, the recycle stream, and a non-reactive co-feed to the catalyst flow, a volume ratio of the recycle stream to the non-reactive co-feed being between 0.2 and 10.

Embodiment 7. The method of any of the above embodiments, wherein the recycle stream comprises 90 wt % or more of 177° C.-compounds, or wherein the recycle stream comprises 90 wt % or more of compounds having a boiling range of 30° C. to 177° C.

Embodiment 8. The method of any of the above embodiments, wherein the recycle stream comprises 20 wt % or more of olefins relative to a weight of the recycle stream, or wherein the recycle stream comprises 20 wt % or more of $C_{5+}$ olefins relative to a weight of the recycle stream, or wherein the recycle stream comprises 20 wt % or more of $C_{6+}$ olefins relative to a weight of the recycle stream.

Embodiment 9. The method of any of the above embodiments, wherein a molar ratio of olefins in the olefin-containing feed to olefins in the recycle stream is 0.5 to 2.0.

Embodiment 10. The method of any of the above embodiments, wherein the olefin oligomerization conditions comprise an olefin partial pressure in the first moving bed reactor of 200 psig to 300 psig (1.4 MPa-g to 2.1 MPa-g).

Embodiment 11. The method of any of the above embodiments, wherein the olefin oligomerization conditions comprise a partial pressure of olefins from the feed in the first moving bed reactor of 200 psig to 300 psig (1.4 MPa-g to 2.1 MPa-g).

Embodiment 12. The method of any of the above embodiments, further comprising: separating spent catalyst from the second effluent; and passing the spent catalyst into a regenerator to form regenerated catalyst, wherein at least a portion of the catalyst flow comprises regenerated catalyst.

Embodiment 13. The method of any of the above embodiments, wherein exposing the olefin-containing feed and the recycle stream to the catalyst flow in the plurality of serially connected moving bed reactors comprises: passing the catalyst flow comprising a catalyst into a first moving bed reactor of the plurality of serially connected moving bed reactors; exposing the feed and the recycle stream to the catalyst flow in the first moving bed reactor under first olefin oligomerization conditions to form a partially reacted effluent, a temperature differential between the first reactor feed inlet and the first reactor effluent outlet being 85° C. or less; stripping the catalyst flow with a first stripping fluid to separate at least a portion of the first partially reacted effluent from the catalyst flow, the at least a portion of the first partially reacted effluent comprising a liquid phase effluent portion and a vapor phase effluent portion; passing the stripped catalyst flow into a second moving bed reactor of the plurality of serially connected moving bed reactors; passing the liquid phase effluent portion into the second moving bed reactor as a substantially axial flow; and exposing the vapor phase effluent portion to the stripped catalyst flow in the presence of the liquid effluent portion in the second moving bed reactor under second olefin oligomerization conditions to form the oligomerized effluent.

Embodiment 14. The method of Embodiment 13, wherein the stripped catalyst flow into the second moving bed reactor forms a catalyst bed having a top surface comprising one or more cones at an angle of repose of the catalyst in the stripped catalyst flow, and wherein passing the liquid phase effluent portion into the second moving bed reactor comprises contacting at least a portion of the liquid phase effluent portion with the one or more cones.

Embodiment 15. A distillate boiling range product made according to any of the above embodiments.

Additional Embodiment A. The method of Embodiment 13 or 14, wherein the vapor flow within the second moving bed reactor comprises an axial vapor flow, or wherein the vapor flow within the second moving bed reactor comprises a radial vapor flow.

Additional Embodiment B. The method of Embodiment 13 or 14, wherein the plurality of serially connected moving bed reactors comprises a vertical stack, and wherein the stripped catalyst flow is passed into the second reactor without passing through a catalyst flow controller.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A method for upgrading a feed to form distillate boiling range compounds, comprising:
    passing a catalyst flow comprising an olefin oligomerization catalyst into a first moving bed reactor of a plurality of serially connected moving bed reactors, the olefin oligomerization catalyst comprising a 1-D 10-member ring zeolite;
    exposing an olefin-containing feed comprising $C_3$-$C_8$ olefins and a recycle stream comprising at least 20 wt % $C_{5+}$ olefins to the catalyst flow in the plurality of moving bed reactors under olefin oligomerization conditions to form an oligomerized effluent, the olefin oligomerization conditions comprising substantially adiabatic operation of the plurality of moving bed reactors and an average reactor temperature of 170° C.-190° C.;
    separating the oligomerized effluent to form a distillate boiling range fraction and one or more lower boiling fractions, the one or more lower boiling fractions comprising the recycle stream;
    wherein exposing the olefin-containing feed and the recycle stream to the catalyst flow in the plurality of serially connected moving bed reactors comprises:
    passing the catalyst flow comprising a catalyst into a first moving bed reactor of the plurality of serially connected moving bed reactors;
    exposing the feed and the recycle stream to the catalyst flow in the first moving bed reactor under first olefin oligomerization conditions to form a partially reacted effluent, a temperature differential between the first reactor feed inlet and the first reactor effluent outlet being 85° C. or less;
    stripping the catalyst flow with a first stripping fluid to separate at least a portion of the first partially reacted effluent from the catalyst flow, the at least a portion of the first partially reacted effluent comprising a liquid phase effluent portion and a vapor phase effluent portion;
    passing the stripped catalyst flow into a second moving bed reactor of the plurality of serially connected moving bed reactors;
    passing the liquid phase effluent portion into the second moving bed reactor as a substantially axial flow; and
    exposing the vapor phase effluent portion to the stripped catalyst flow in the presence of the liquid effluent portion in the second moving bed reactor under second olefin oligomerization conditions to form the oligomerized effluent.

2. The method of claim 1, wherein the olefin oligomerization conditions comprise a temperature differential across a moving bed reactor of 85° C. or less.

3. The method of claim 1, wherein the olefin oligomerization catalyst comprises ZSM-48.

4. The method of claim 1, wherein the olefin-containing feed comprises 60 wt % or more of $C_3$-$C_5$ olefins relative to a weight of olefins in the olefin-containing feed.

5. The method of claim 1, wherein the olefin-containing feed comprises 5.0 wt % or less of $C_2$ olefins relative to a weight of olefins in the olefin-containing feed, or wherein the olefin-containing feed comprises 5.0 wt % or less of water relative to a weight of the olefin-containing feed, or a combination thereof.

6. The method of claim 1, wherein exposing the olefin-containing feed and the recycle stream to the catalyst flow comprises exposing the olefin-containing feed, the recycle stream, and a non-reactive co-feed to the catalyst flow.

7. The method of claim 6, wherein a volume ratio of the recycle stream to the non-reactive co-feed is between 0.2 and 10.

8. The method of claim 1, wherein the recycle stream comprises 90 wt % or more of 177° C.-compounds.

9. The method of claim 1, wherein the recycle stream comprises 90 wt % or more of compounds having a boiling range of 30° C. to 177° C.

10. The method of claim 1, wherein the recycle stream comprises 20 wt % or more of olefins relative to a weight of the recycle stream.

11. The method of claim 1, wherein the recycle stream comprises 20 wt % or more of $C_{5+}$ olefins relative to a weight of the recycle stream.

12. The method of claim 1, wherein the recycle stream comprises 20 wt % or more of $C_{6+}$ olefins relative to a weight of the recycle stream.

13. The method of claim 1, wherein a molar ratio of olefins in the olefin-containing feed to olefins in the recycle stream is 0.5 to 2.0.

14. The method of claim 1, wherein the olefin oligomerization conditions comprise an olefin partial pressure in the first moving bed reactor of 200 psig to 300 psig (1.4 MPa-g to 2.1 MPa-g).

15. The method of claim 1, wherein the olefin oligomerization conditions comprise a partial pressure of olefins from the feed in the first moving bed reactor of 200 psig to 300 psig (1.4 MPa-g to 2.1 MPa-g).

16. The method of claim 1, further comprising:
separating spent catalyst from the second effluent; and
passing the spent catalyst into a regenerator to form regenerated catalyst,
wherein at least a portion of the catalyst flow comprises regenerated catalyst.

17. The method of claim 1, wherein the stripped catalyst flow into the second moving bed reactor forms a catalyst bed having a top surface comprising one or more cones at an angle of repose of the catalyst in the stripped catalyst flow, and wherein passing the liquid phase effluent portion into the second moving bed reactor comprises contacting at least a portion of the liquid phase effluent portion with the one or more cones.

18. The method of claim 1, wherein the vapor flow within the second moving bed reactor comprises an axial vapor flow, or wherein the vapor flow within the second moving bed reactor comprises a radial vapor flow.

19. The method of claim 1, wherein the plurality of serially connected moving bed reactors comprises a vertical stack, and wherein the stripped catalyst flow is passed into the second reactor without passing through a catalyst flow controller.

* * * * *